United States Patent [19]

Bugaut et al.

[11] 4,185,958
[45] Jan. 29, 1980

[54] COMPOSITIONS BASED ON DIRECT DYESTUFFS CONTAINING A 2,5-DIHYDROXYPHENYLCARBOXYLIC ACID OR A SALT THEREOF

[76] Inventors: Andrée Bugaut, 7, rue des Abondances, 92100 Boulogne-Billancourt; Jean-Francois Grollier, 19, rue de Dantzig, 75015 Paris; Jean-Jacques Vandenboosche, 6, rue Leon Richet, 93600 Aulnay-sous-Bois, all of France

[21] Appl. No.: 935,014

[22] Filed: Aug. 18, 1978

[30] Foreign Application Priority Data

Aug. 19, 1977 [LU] Luxembourg ............................ 77995

[51] Int. Cl.$^2$ .............................................. A61K 7/13
[52] U.S. Cl. ............................................ 8/10.1; 8/10; 8/92; 544/161; 562/465; 562/478

[58] Field of Search ........................... 8/10, 10.1, 92

[56] References Cited

U.S. PATENT DOCUMENTS

| | | | |
|---|---|---|---|
| 3,464,778 | 9/1969 | Berth et al. | 8/10.1 |
| 3,480,377 | 11/1969 | Lyons | 8/10.1 |
| 3,488,138 | 1/1970 | Iscowitz | 8/10.1 |
| 3,565,571 | 2/1971 | Reese et al. | 8/10.1 |
| 3,642,423 | 2/1972 | Bil et al. | 8/10.1 |
| 3,893,805 | 7/1975 | Dellian et al. | 8/92 X |

*Primary Examiner*—James O. Thomas, Jr.
*Assistant Examiner*—Vera C. Clarke
*Attorney, Agent, or Firm*—Fleit & Jacobson

[57] ABSTRACT

A composition suitable for dyeing keratin fibres, especially human hair, is provided comprising a direct dyestuff and, as a levelling agent, a 2,5-dihydroxyphenylcarboxylic acid or a salt thereof.

23 Claims, No Drawings

COMPOSITIONS BASED ON DIRECT DYESTUFFS CONTAINING A 2,5-DIHYDROXYPHENYLCARBOXYLIC ACID OR A SALT THEREOF

The present invention relates to dyeing compositions which are intended for dyeing keratin fibres, and in particular for dyeing human hair which have been bleached and optionally permanently waved, the said composition containing a 2,5-dihydroxyphenylcarboxylic acid or one of its salts.

Persons who possess a naturally deep-coloured head of hair and who desire a head of hair with a lighter shade have to undergo a powerful bleaching treatment followed by re-dyeing. This powerful bleaching treatment is generally carried out by means of very strong oxidising agents such as concentrated ammoniacal solutions of hydrogen peroxide which are most frequently mixed with per-salts. A powerful bleaching treatment of this kind gives rise to yellowish or orange shades which are not very aesthetic. This result is all the less aesthetic when the initial colour of the natural hair is deeper. In practice, hair which is bleached in this way is therefore always re-dyed.

This dyeing can be carried out in accordance with several techniques. One of these techniques consists in applying, to the bleached hair, a dye based on so-called oxidative dyestuffs which develop their colour on the hair after having been mixed with ammoniacal hydrogen peroxide.

Hair which has already been bleached undergoes an additional undesirable change caused by the ammoniacal oxidising mixture. Furthermore, many persons have difficulty in tolerating the application of a dye of this type on a scalp which has already been irritated by bleaching. In addition, since so-called oxidative dyestuffs are applied to very sensitised hair, it is necessary to use particularly low concentrations of dyestuffs if it is desired to obtain shades which are not too deep. However, the low concentrations of dyestuffs used results in shades which are very luminous but unfortunately have only mediocre resistance to light and shampoo.

A further technique involves the use of direct dyestuffs such as nitro dyestuffs, disperse dyestuffs, metallised dyestuffs, acid dyestuffs and basic dyestuffs, mixed with a levelling agent such as ascorbic acid or thiourea. This levelling agent acts, inter alia, as a reducing agent and removes the traces of oxidising agent which are present on the hair after bleaching. These traces of oxidising agent can destroy the dyestuff applied, giving rise to unevennesses of coloration, particularly around the roots which have just been bleached.

However, these proposed expedients exhibit disadvantages. In fact, ascorbic acid, proposed in French Pat. No. 1,408,167, is unstable at the pH values which are usually employed for dyeing, so that it must be introduced at the moment of application. Furthermore, the harmless nature of thiourea, described in French Pat. No. 1,447,175, is questionable.

The object of the present invention is to overcome the abovementioned disadvantages of such levelling agents. This is achieved, according to the present invention, by using, in place of these compounds, an acid or one of its salts, of the formula:

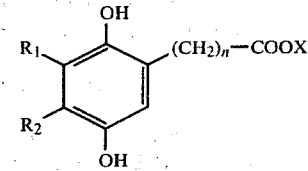

in which $R_1$ and $R_2$ are identical or different and denote hydrogen or a straight- or branched-chain lower $C_1$–$C_4$ alkyl group, preferably a methyl, ethyl or propyl group, X denotes hydrogen, an alkali metal such as sodium or potassium, ammonium, or a quaternary alkanolamine radical such as a monoethanolamine, diethanolamine or triethanolamine radical, and n is 0 or an integer from 1 to 4.

The present invention therefore provides dyeing compositions for keratin fibres, and in particular for human hair which has been bleached and optionally permanently waved, which compositions comprise at least one direct dyestuff and additionally comprise an acid or one of its salts, of formula (I). Typical such acids include gentisic, homogentisic, 2-[(2',5'-dihydroxy-4'-methyl)phenyl]-acetic, 3-[(2',5'-dihydroxy)phenyl]propionic, 3-[(2',5'-dihydroxy-4'-methyl)phenyl]propionic and 3-[(2',5'-dihydroxy-3',4'-dimethyl)phenyl]acetic acids.

The present invention further provides a process for dyeing hair, which employs the abovementioned dyeing compositions. Typically this process involves applying the composition to the freshly bleached hair, allowing it to act on the hair for, say, 5 to 30 minutes and then rinsing and drying the hair.

The compounds used in accordance with the invention exhibit several advantages. They have a good solubility in the carriers which are usually employed. They possess a good compatibility with the direct dyestuffs which are generally used. Under these conditions, the preservation of the dyeing compositions is good.

When the compounds of the formula (I) above are used in the dyeing compositions of the invention, they have the effect of masking the traces of oxidising agent remaining on the hair after bleaching with a powerful oxidising agent, and make it possible to obtain a very uniform dyeing.

Concentrated ammoniacal solutions of hydrogen peroxide, most frequently mixed with per-salts such as ammonium persulphate, sodium persulphate or potassium persulphate, may be mentioned as the powerful oxidising agent.

According to the invention, the concentration of the acid of the formula (I) or its salts is generally 0.1 to 10% by weight, and preferably 0.5 to 3% by weight relative to the total weight of the dyeing compositions.

The dyeing compositions according to the invention can contain all types of direct dyestuffs such as nitrobenzene derivatives, azo dyestuffs or anthraquinone dyestuffs. These dyestuffs can be disperse, metallised, acid or basic dyestuffs.

The name "direct dyestuff" as used herein denotes coloured substances which, when applied in solution to the hair, impart their own colorations thereto.

The nitrobenzene derivatives can be nitrophenylenediamines, nitroaminophenols, dinitroaminophenols, dinitroaminobenzenes, nitroaminobenzenes, such as those described in U.S. patent application Ser. Nos. 628,999 filed on Nov. 5, 1975 now abandoned in favor of a presently pending continuation-in-part application Ser. No. 682,798 and 789,444 filed on Apr. 20, 1977, now U.S. Pat. 4,125,601, and also nitrodiphenylamines.

Specific examples include: 1-hydroxy-2-amino-4,6-dinitrobenzene, 2-nitro-p-phenylenediamine, 1-amino-2-nitro-4-(N-methylamino)-benzene, 1-hydroxy-2-amino-5-nitrobenzene, 4-nitro-m-phenylenediamine, 1-methoxy-3-nitro-4-[N-($\beta$-hydroxyethyl)-amino]-benzene, 1-($\beta$-hydroxyethyloxy)-3-nitro-4-aminobenzene, 1-methoxy-2-[N-($\beta$-hydroxyethyl)amino]-5-nitrobenzene, 1-amino-2-nitro-4-[N-($\beta$-hydroxyethyl)-amino]-benzene, 1-(N-methylamino)-2-nitro-4-[N,N-bis-($\beta$-hydroxyethyl)-amino]-benzene, 1-(N-methylamino)-2-nitro-4-[N-methyl-N-($\beta$-hydroxyethyl)-amino]-benzene, 1-hydroxy-3-nitro-4-[N-($\beta$-hydroxyethyl)amino]-benzene, 1-hydroxy-2,6-dimethyl-3-nitro-4-[N-($\beta$-hydroxyethyl)-amino]-benzene, 4-nitro-o-phenylenediamine, 1-hydroxy-2-amino-4-nitrobenzene, 1-hydroxy-2-nitro-4-aminobenzene, 1,4-bis-[N-($\beta$-hydroxyethyl)-amino]-2-nitrobenzene, 1-amino-2-[N-($\beta$-hydroxyethyl)-amino]-5-nitrobenzene, 1,4,4-tris-N-($\beta$-hydroxyethyl)-2-nitro-p-phenylenediamine, 1-($\beta$-hydroxyethyloxy)-2-[N-($\beta$-hydroxyethyl)amino]-5-nitrobenzene, 1-amino-2-[tris-(hydroxymethyl)-methyl]-amino-5-nitrobenzene, 1-[N-($\beta$-hydroxyethyl)-amino]-2-nitrobenzene, 1,4,4-tris-N-($\beta$-hydroxyethyl)-3-nitro-p-phenylenediamine, 2-nitro-4'-[bis($\beta$-hydroxyethyl)-amino]-diphenylamine, 2-nitro-4'-hydroxydiphenylamine, 2-nitro-4-aminodiphenylamine, 1-amino-3-nitro-4-[N-($\beta$-hydroxyethyl)-amino]-benzene, 1-hydroxy-2-[N-bis-($\beta$-hydroxyethyl)-amino]-5-nitrobenzene and 1-amino-2-nitro-4-[N-($\beta$-hydroxyethyl)-amino]-5-chlorobenzene.

The disperse dyestuffs are sparingly water-soluble dyestuffs. Most of these dyestuffs are azo or anthraquinone dyestuffs.

Specific examples include the following dyestuffs which are denoted by their name in the Colour Index: CI Disperse Violet 15, CI Disperse Violet 4 (61.105), CI Disperse Red 11 (62.015), CI Disperse Yellow 1 (10.345), CI Disperse Blue 1 (64.500), CI Disperse Blue 2, CI Disperse Black 5 and CI Disperse Black 22.

The acid dyestuffs contain acid groups such as sulphonic acid and carboxylic acid groups.

Specific examples include the following acid dyestuffs which are denoted by their name in the Colour Index: CI Acid Red 35 (18.065), CI Acid Violet 43 (60.730) and CI Acid Orange 24 (20.170).

The basic dyestuffs can be, for example, CI basic Violet 10 (45.170), 1-(N-methylamino)-4-[N-(3-aminopropyl)-amino]-anthraquinone hydrochloride, 1-[N-(3-aminopropyl)-amino]-anthraquinone hydrochloride and 2-[N-(2-aminoethyl)-amino]-anthraquinone hydrochloride, described in French Pat. No. 1,516,943.

Other direct dyestuffs, for example metallised dyestuffs, can also be included in the compositions of the invention, such as the following dyestuffs which are denoted by their name in the Colour Index: CI Acid Violet 56 (16.055), CI Acid Red 184 (15.685) and CI Acid Blue 170.

The concentrations of the direct dyestuffs in the dyeing compositions according to the invention are generally 0.005 to 5% by weight, and preferably 0.01 to 3% by weight, relative to the total weight of the dyeing compositions.

The dyeing compositions according to the invention are suitably in the form of aqueous solutions which can contain, in addition to the direct dyestuffs and the acid compounds, a solvent, for example an alcohol such as ethyl alcohol or isopropyl alcohol, or a glycol or glycol ether such as, propylene glycol, the monoethyl or monobutyl ether of ethylene glycol, carbitol or butylcarbitol, in amounts of 0.5 to 20% by weight and preferably 2 to 10% by weight.

They can also contain anionic, cationic, non-ionic or amphoteric surface-active agents, generally in an amount up to 50% by weight.

Specific examples of anionic surface-active agents which can be used by themselves or in a mixture are the alkali metal salts, magnesium salts, ammonium salts, amine salts or alkanolamine salts of the following compounds: alkyl-sulphates, alkyl-ether-sulphates and oxyethylenated alkylamide-sulphates optionally alkylsulphonates, alkylamidesulphonates and alpha-olefine-sulphonates, alkylsulphosuccinates and alkyl-ether-sulphosuccinates, alkylsulphoacetates, the alkyl radicals in these compounds having a linear $C_{12}$ to $C_{18}$ chain, fatty acids such as lauric, myristic, oleic, ricinoleic, palmitic and stearic acids, acids derived from copra oil of from hydrogenated copra oil, and carboxylic acids or polyglycol ethers.

Among the cationic surface-active agents which can be used by themselves or in a mixture, there may be mentioned, in particular: salts of fatty amines, quaternary ammonium salts such as alkyldimethylbenzylammonium, alkyltrimethylammonium, alkyldimethylhydroxyethylammonium and dimethyldistearylammonium chlorides and bromides, alkylpyridinium salts and imidazoline derivatives.

Compounds of cationic character, such as amine oxides may also be mentioned.

Suitable non-ionic surface-active agents which can optionally be used as a mixture with the abovementioned anionic and/or cationic surface-active agents, include: the products resulting from the condensation of a monoalcohol, an $\alpha$-diol, an alkylphenol or an amide with glycidol, for example the compounds of the formula R—CHOH—CH$_2$—O—(CH$_2$—CHOH—CH$_2$—O)$_{n_2}$H in which R denotes an aliphatic, cycloaliphatic or arylaliphatic radical having from 7 to 21 carbon atoms, and mixtures thereof, it being possible for the aliphatic chains to contain ether, thioether and hydroxymethylene group, and $n_2$ being an integer such that $1 \leq n_2 \leq 10$, and the compounds of the formula RO$-$(C$_2$H$_3$O(CH$_2$OH))$_{n_3}$H in which R denotes an alkyl, alkenyl or alkylaryl radical having 8 to 22 carbon atoms and $1 \leq n_3 \leq 10$, alcohols, alkylphenols or polyoxyethylenated or polyglycerolated fatty acids having a linear $C_8$ to $C_{18}$ fatty chain, the products resulting from the condensation of ethylene oxide and propylene oxide with fatty alcohols, polyoxyethylenated fatty amides and polyoxyethylenated fatty amines.

Among the amphoteric surface-active agents which can be used, there may be mentioned, in particular: alkylamino-mono- and -di-propionates, betaines such as N-alkylbetaines, N-alkylsulphobetaines and N-alkylaminobetaines, the alkyl radical containing from 1 to 22 carbon atoms, and cycloimidinium compounds such as alkylimidazolines.

The concentration of surface-active agent in the dyeing compositions according to the invention is generally 0.1 or 0.5 to 50% by weight, and preferably 1 to 20% by weight, relative to the total weight of the composition.

The dyeing compositions of the invention can also contain fatty amides such as the mono- and diethanolamides of acids derived from copra, of lauric acid or of oleic acid, suitably at concentrations of 0.5 to 10% by weight.

They can additionally contain higher fatty alcohols ($C_{10}$–$C_{22}$) such as oleyl, myristyl, cetyl, stearyl and isostearyl alcohols, at concentrations of, say, 0.5 to 10% by weight.

They can also contain thickeners such as sodium alginate or gum arabic, or cellulose derivatives such as methylcellulose, hydroxymethylcellulose, hydroxyethylcellulose or hydroxypropylcellulose, in concentrations of, say, 0.5 to 15% by weight.

In addition to the abovementioned ingredients, the dyeing compositions according to the invention can contain adjuvants such as perfumes, preservatives and sequestering agents.

The pH of the dyeing compositions according to the invention can be adjusted with alkaline agents such as monoethanolamine, diethanolamine, triethanolamine, ammonia, ammonium carbonate, potassium carbonate or sodium carbonate, or sodium hydroxide, or with acidifying agents such as phosphoric, hydrochloric, tartaric, acetic, lactic or citric acid. This pH is suitably from 5 to 10 but is advantageously from 6 to 9.5 and preferably from 7 to 9.

The dyeing compositions according to the invention can be in various customary forms such as thickened liquids, foaming liquids and aerosol foams.

When applied to freshly bleached hair for 5 to 30 minutes, the dyeing compositions of the invention make it possible to obtain a uniform coloration from the tip to the roots, as can be observed after rinsing the head of hair.

The compounds of the formula (I) in which n is from 1 to 4, can be prepared in accordance with two known processes A and B, depending on whether n=1 or 2 or n=3 or 4.

Process A makes it possible to obtain the compounds in which n=1 or 2 and comprises the following steps:

(1) Friedel/Crafts reaction on the compounds (II)

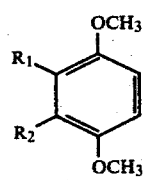

in the presence of e.g. $AlCl_3$, using acetyl or propionyl chloride to obtain the compounds (III):

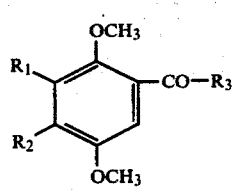

in which $R_3 = CH_3$ or $C_2H_5$.

(2) Willgerodt reaction (for example with sulphur and morpholine) on the compounds (III) to obtain the aceto- or propiono-thiomorpholides (IV)

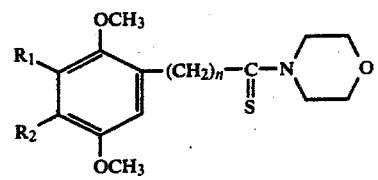

in which n=1 or 2.

(3) Alkaline hydrolysis of the compounds (IV) to obtain the compounds (V):

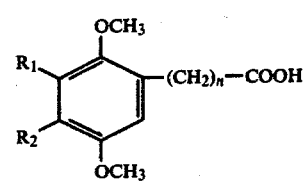

in which n=1 or 2.

(4) Demethoxylation of the compounds (V), using hydrobromic acid to obtain the acids (I):

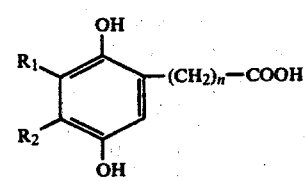

in which n=1 or 2.

Process B for the preparation of compounds (I) in which n=3 or 4 comprises the following steps:

(1) Action of succinic or glutaric anhydride, in the presence of $AlCl_3$, on the compounds (II):

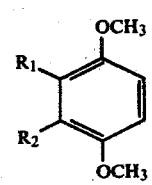

to obtain the comounds (VI):

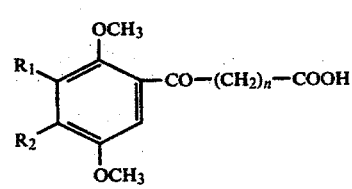

in which n=2 or 3.

(2) Reduction of the compounds (VI) by the Clemmensen method (Zn amalgam, HCl) or, preferably, using hydrazine to obtain the compounds (V):

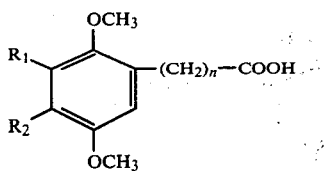

in which n=3 or 4.

(3) Demethoxylation of the compounds (V), using hydrobromic or hydriodic acid to obtain the acids (I):

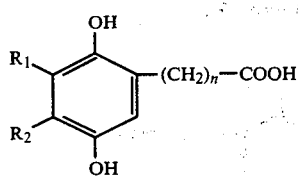

in which n=3 or 4.

The acids of the formula (I), obtained in accordance with processes A and B above, can then be converted, in known manner, into alkali metal, ammonium or alkanolamine salts.

The compounds of formula (I) indicated in which n is from 1 to 4 and which contain at least one substituent on the phenyl nucleus, that is to say the compounds in which at least one of the symbols $R_1$ and $R_2$ denotes a straight- or branched-chain $C_1$-$C_4$ lower alkyl group are novel and are described and claimed in our Application Ser. No. 934,830 filed Aug. 18, 1978. The following Examples illustrate the preparation of some of the novel compounds used in the compositions of the present invention.

REFERENCE EXAMPLE 1

Preparation of 2-(2',5'-dihydroxy-4'-methylphenyl)-acetic acid

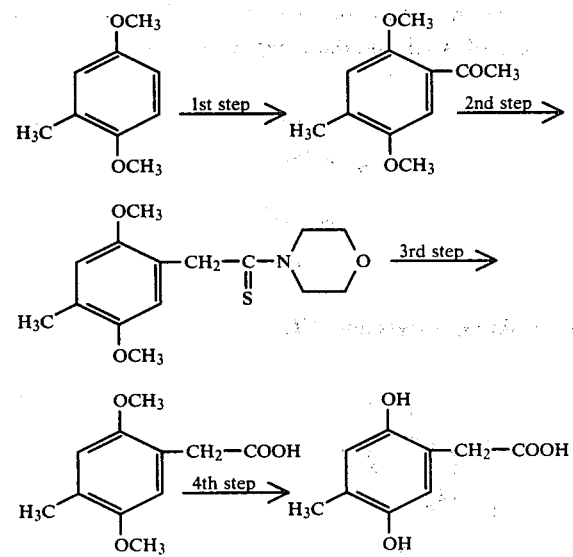

1st step: Preparation of 2,5-dimethoxy-4-methylacetophenone.

1 mol (152 g) of 2,5-dimethoxytoluene is introduced, whilst stirring, into 230 ml of acetyl chloride at −10° C. 160 g of aluminium chloride are then added in the course of 3 hours, whilst stirring and keeping the temperature of the reaction medium at between −10° and 0° C. When the addition has ended, the mixture is stirred for a further 3 hours at between −10° and 0° C. The reaction medium is then poured onto 1 kg of crushed ice to which 110 ml of hydrochloric acid (d=1.19) have been added. After a few hours, the reaction product which has precipitated is filtered off. After washing with water, a 2 N solution of sodium hydroxide and then again with water, the 2,5-dimethoxy-4-methylacetophenone is recrystallized from ethanol. After drying in vacuo, it melts at 75° C.

| Analysis | Calculated for $C_{11}H_{14}O_3$ | Found |
|---|---|---|
| C% | 68.04 | 68.09 |
| H% | 7.21 | 7.00 |

2nd step: Preparation of (2,5-dimethoxy-4-methylphenyl)acetothiomorpholide.

0.7 mol (136 g) of 2,5-dimethoxy-4-methylacetophenone is heated under reflux for 8 hours in the presence of 1.05 mol (33.6 g) of sulphur in 92 g of morpholine. The reaction medium is then poured into 500 g of ice-cooled water. The reaction product precipitates in the form of a gum. After recrystallisation from ethanol and then acetone and after drying in vacuo, the product melts at 121° C.

| Analysis | Calculated for $C_{15}H_{21}SNO_3$ | Found |
|---|---|---|
| C% | 61.02 | 60.82 |
| H% | 7.12 | 7.30 |
| S% | 10.85 | 11.19 |
| N% | 4.75 | 4.99 |

3rd step: Preparation of 2-(2',5'-dimethoxy-4'-methylphenyl)acetic acid.

0.54 mol (160 g) of (2,5-dimethoxy-4-methylphenyl)acetothiomorpholide is heated under reflux for 4 days in 700 ml of an aqueous-ethanolic solution (75% of ethanol, 25% of $H_2O$) containing 4 mols (160 g) of sodium hydroxide in solution. The alcohol is then driven off in vacuo, 700 ml of water are added and the reaction medium is again heated to the reflux temperature and filtered at the boil in order to remove a small amount of insoluble material. After cooling, the 2-(2',5'-dimethoxy-4'-methylphenyl)acetic acid is precipitated by adding hydrochloric acid. The white precipitate obtained is filtered off, washed with water and recrystallised from ethanol. After drying in vacuo, it melts at 128° C.

| Analysis | Calculated for $C_{11}H_{14}O_4$ | Found |
|---|---|---|
| C% | 62.86 | 62.93 |
| H% | 6.66 | 6.65 |

4th step: Preparation of 2-(2',5'-dihydroxy-4'-methylphenyl)acetic acid.

0.285 mol (60 g) of 2-(2',5'-dimethoxy-4'-methylphenyl)-acetic acid is heated under reflux for 5 hours in 480 ml of 48% strength hydrobromic acid.

After cooling, the acid obtained is filtered off and, after recrystallisation from alcohol and drying in vacuo, melts at 178° C.

| Analysis | Calculated for $C_9H_{10}O_4$ | Found |
|---|---|---|
| C% | 59.34 | 59.30 |
| H% | 5.50 | 5.78 |

REFERENCE EXAMPLE 2

Preparation of 2-(2',5'-dihydroxy-3',4'-dimethylphenyl)acetic acid

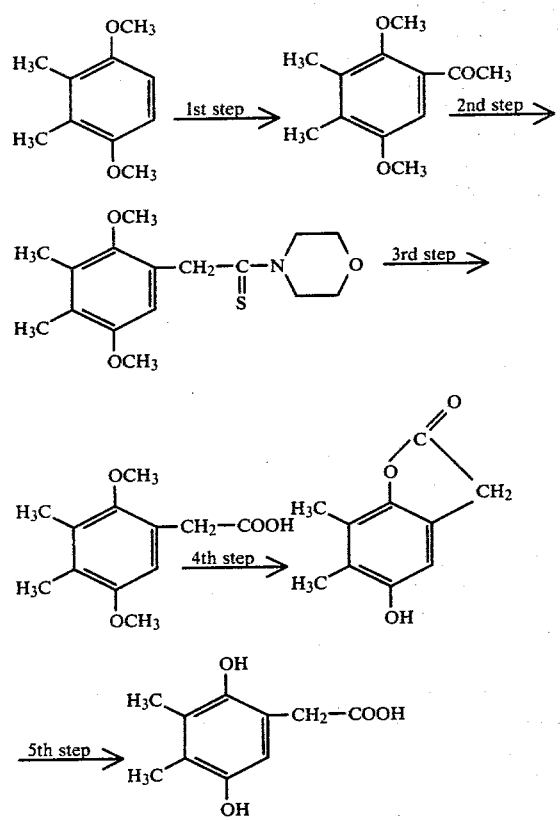

1st step: Preparation of 2,5-dimethoxy-3,4-dimethylacetophenone.

0.15 mol (25 g) of 2,3-dimethyl-1,4-dimethoxybenzene is introduced, whilst stirring, into 35 ml of acetyl chloride at $-10°$ C. 24 g of aluminium chloride are then added gradually, whilst keeping the temperature at between $-10°$ and $-5°$ C. When the addition has ended, the reaction medium is left to stand for 3 hours at about $-5°$ C. and is then poured onto 170 g of crushed ice to which 17 ml of hydrochloric acid (d=1.19) have been added. The thick oil which precipitates is separated off by decantation. This oil distils at between 106° and 107° C. under a pressure of 0.1 mm Hg.

| Analysis | Calculated for $C_{12}H_{16}O_3$ | Found |
|---|---|---|
| C% | 69.23 | 69.30 |
| H% | 7.69 | 7.64 |

2nd step: Preparation of (2,5-dimethoxy-3,4-dimethylphenyl)acetothiomorpholide.

0.33 mol (69.3 g) of 2,5-dimethoxy-3,4-dimethylacetophenone is heated under reflux for 10 hours in the presence of 0.5 mol (16 g) of sulphur in 43.5 g of morpholine. The reaction medium is then poured onto 250 g of crushed ice. The reaction product precipitates in the form of a gum.

The gummy product is treated with 100 ml of ethanol under reflux. The mixture is filtered at the boil. On cooling, the acetothiomorpholide obtained crystallises. After recrystallisation from acetone and drying in vacuo, it melts at 108° C.

| Analysis | Calculated for $C_{16}H_{23}NSO_3$ | Found |
|---|---|---|
| C% | 62.13 | 62.12 |
| H% | 7.44 | 7.30 |
| N% | 4.53 | 4.67 |
| S% | 10.36 | 10.66 |

3rd step: Preparation of 2-(2',5'-dimethoxy-3',4'-dimethylphenyl)-acetic acid.

0.217 mol (67 g) of (2,5-dimethoxy-3,4-dimethylphenyl)-acetothiomorpholide is heated under reflux for 10 hours in 400 ml of an aqueous-ethanolic solution (65% of ethanol, 35% of $H_2O$) containing 1.7 mol (68 g) of sodium hydroxide. The alcohol is driven off in vacuo, 300 ml of water are added and the reaction medium is again heated to the reflux temperature and filtered at the boil in order to remove a small amount of insoluble material. After cooling, the 2-(2',5'-dimethoxy-3',4'-dimethylphenyl)-acetic acid is precipitated by adding hydrochloric acid. The product is filtered off, washed with water, recrystallised from alcohol and dried in vacuo. It melts at 109° C.

| Analysis | Calculated for $C_{12}H_{16}O_4$ | Found |
|---|---|---|
| C% | 64.28 | 64.08 |
| H% | 7.14 | 7.03 |

4th and 5th steps: Preparation of 2-(2',5'-dihydroxy-3',4'-dimethylphenyl)-acetic acid with isolation of the intermediate lactone.

0.3 mol (67.2 g) of 2-(2',5'-dimethoxy-3',4'-dimethylphenyl)-acetic acid is heated under reflux for 1 hour in 400 ml of hydriodic acid to which 130 ml of acetic acid have been added, the fractions having boiling points below 70° C. being removed by distillation as they are formed. The reflux temperature of the reaction medium gradually reaches 115° C.

From 95° C., the reaction product precipitates in the form of a lactone in the reaction medium.

The lactone is filtered off and washed with water. After drying in vacuo, it melts at 220° C.

The lactone obtained is dissolved in 100 ml of a 10 N solution of sodium hydroxide to which 20 g of sodium sulphite have been added. The solution is heated for 20 minutes at 90° C. It is filtered hot. After cooling, the filtrate is acidified to pH 2 using 20% strength sulphuric acid and the reaction product is then extracted with ether. The ether is driven off in vacuo. The crude product thus obtained is recrystallised from a mixture of alcohol, chloroform and petroleum ether. After drying in vacuo, it melts at 176° C.

| Analysis | Calculated for $C_{10}H_{12}O_4$ | Found |
|---|---|---|
| C% | 61.22 | 61.28 |
| H% | 6.12 | 6.29 |

REFERENCE EXAMPLE 3

Preparation of 3-(2',5'-dihydroxy-4'-methylphenyl)-propionic acid

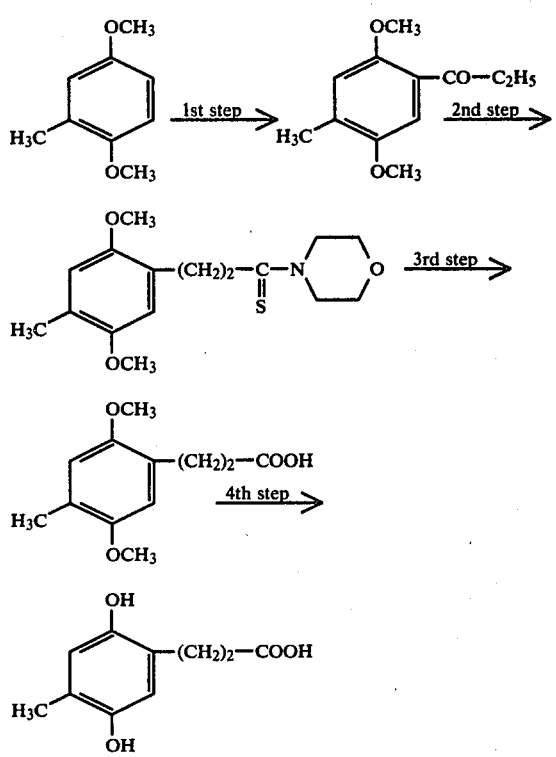

1st step: Preparation of 2,5-dimethoxy-4-methylpropiophenone.

0.3 mol (50 g) of 2,5-dimethoxytoluene is introduced, whilst stirring, into 70 ml of propionyl chloride at −10° C. 48 g of aluminium chloride are added in the course of 3 hours, whilst stirring and keeping the temperature at about −10° C. When the addition has ended, the mixture is stirred for a further 3 hours at this temperature. The reaction medium is then poured onto 1 kg of crushed ice to which 33 ml of hydrochloric acid (d: 1.19) have been added.

The reaction medium is left to stand for a few hours and the product obtained is then filtered off. After washing with water, a 2 N solution of sodium hydroxide and again with water, the product is recrystallised from alcohol. After drying, it melts at 76° C.

| Analysis | Calculated for $C_{12}H_{16}O_3$ | Found |
|---|---|---|
| C% | 69.23 | 69.03 |
| H% | 7.69 | 7.52 |

2nd step: Preparation of (2,5-dimethoxy-4-methylphenyl)propionothiomorpholide.

1 mol (208 g) of 2,5-dimethoxy-4-methylpropiophenone is heated under reflux for 8 hours in the presence of 1.5 mol (48 g) of sulphur in 131 g of morpholine. The reaction medium is then poured into 800 g of ice-cooled water. The reaction product precipitates and is filtered off and dissolved in 1 liter of acetone under reflux. The solution is filtered. After cooling, the propionothiomorpholide precipitates in the form of crystals. It is filtered off and dried in vacuo. It melts at 156° C.

| Analysis | Calculated for $C_{16}H_{23}NSO_3$ | Found |
|---|---|---|
| C% | 62.13 | 61.94 |
| H% | 7.44 | 7.55 |
| N% | 4.53 | 4.61 |
| S% | 10.36 | 10.50 |

3rd step: Preparation of 3-(2',5'-dimethoxy-4'-methylphenyl)propionic acid.

0.18 mol (58 g) of (2,5-dimethoxy-4-methylphenyl)-propionothiomorpholide is heated under reflux for 8 hours in 350 ml of an aqueous-ethanolic solution (65% of ethanol, 35% of $H_2O$) containing 1.5 mols (60 g) of sodium hydroxide. The alcohol is driven off in vacuo and 250 ml of water are added. The reaction medium is again heated to the reflux temperature and filtered at the boil. After cooling the filtrate, the 3-(2',5'-dimethoxy-4'-methylphenyl)-propionic acid precipitates. It is filtered off, washed with water and recrystallised from alcohol. After drying in vacuo, it melts at 111° C.

| Analysis | Calculated for $C_{12}H_{16}O_4$ | Found |
|---|---|---|
| C% | 64.29 | 64.30 |
| H% | 7.14 | 7.14 |

4th step: Preparation of 3-(2',5'-dihydroxy-4'-methylphenyl)propionic acid.

0.18 mol (40 g) of 3-(2',5'-dimethoxy-4'-methylphenyl)-propionic acid is heated under reflux in 300 ml of 48% strength hydrobromic acid. After cooling, the acid obtained precipitates. It is filtered off, dried and recrystallised from a mixture of ethanol, chloroform and petroleum ether. After drying, it melts at 181° C.

| Analysis | Calculated for $C_{10}H_{12}O_4$ | Found |
|---|---|---|
| C% | 61.22 | 61.17 |
| H% | 6.12 | 6.26 |

The following Examples further illustrate the dyeing compositions of the invention.

EXAMPLE NO. 1

The following dyeing composition is prepared:

| | | |
|---|---|---|
| 1-(N-Methylamino)-2-nitro-4-[N,N-bis-($\beta$-hydroxyethyl)-amino]-benzene | 0.04 | g |
| CI Disperse Violet 4 (61.105) | 0.04 | g |
| CI Disperse Black 5 | 0.005 | g |
| 1-Amino-2-nitro-4-(N-methylamino)-benzene | 0.005 | g |
| Copra diethanolamide | 1.8 | g |
| Lauric acid | 0.9 | g |
| Methyl para-hydroxybenzoate | 0.1 | g |
| Tartaric acid | 0.25 | g |
| Ethylene glycol monobutyl ether | 4 | g |
| Hydroxyethylcellulose sold under the name "Cellosize WP 4400" by Messrs. Union Carbide | 3 | g |
| Homogentisic acid | 1 | g |
| Monoethanolamine q.s.p. pH 8 | | |
| Water q.s.p. | 100 | g |

When applied for 25 minutes to hair which has been bleached beforehand, 100 g of this composition, in the form of a thickened liquid, impart to the head of hair, after rinsing with water, a particularly uniform beige blond shade.

EXAMPLE NO. 2

The following dyeing composition is prepared:

| | | |
|---|---|---|
| 1-(N-Methylamino)-2-nitro-4-[N-methyl-N-($\beta$-hydroxyethyl)-amino]-benzene | 0.1 | g |
| 1-($\beta$-Hydroxyethyloxy)-3-nitro-4-aminobenzene | 0.03 | g |
| Mixture of cetyl/stearyl alcohol and sodium alkyl-sulphate, sold under the name SINNOVAX SX by Messrs. Henkel | 2 | g |
| Linear fatty alcohol ($C_{13}$–$C_{15}$) oxyethyleneated with 2.8 mols of ethylene oxide, sold under the name "Ukanil 25" by Messrs. P.U.K. | 3 | g |
| Linear fatty alcohol ($C_{13}$–$C_{15}$) oxyethyleneated with 7 mols of ethylene oxide, sold under the name "Ukanil 43" by Messrs. P.U.K. | 2 | g |
| Trimethylcetylammonium bromide | 1.5 | g |
| Ethylene glycol monobutyl ether | 10 | g |
| Homogentisic acid | 1 | g |
| Monoethanolamine q.s.p. pH 8 | | |
| Water q.s.p. | 100 | g |

90 g of this mixture and 10 g of the propellant mixture F.114/12 (43/57) are incorporated into an aerosol container.

The product obtained retains good dyeing properties for several months.

About 20 g of this foam are applied to moderately bleached hair. After 15 minutes, the head of hair is rinsed and dried and is uniformly dyed beige blond.

EXAMPLES 3A and 3B

The following dyeing compositions are prepared:

| | 3A | 3B |
|---|---|---|
| 1-(N-Methylamino)-2-nitro-4-[N,N-bis-($\beta$-hydroxyethyl)-amino]-benzene | 0.025g | 0.025g |
| CI Disperse Violet (61.105) | 0.025g | 0.025g |
| CI Disperse Violet 15 | 0.020g | 0.020g |
| CI Disperse Black 22 | 0.002g | 0.002g |
| Copra diethanolamide | 1.8 g | 1.8 g |
| Lauric acid | 0.9 g | 0.9 g |
| Methyl para-hydroxybenzoate | 0.1 g | 0.1 g |
| Tartaric acid | 0.25 g | 0.25 g |
| Ethylene glycol monobutyl ether | 4 g | 4 g |
| Hydroxyethylcellulose sold under the name Cellosize WP 4400 by Messrs. Union Carbide | 3 g | 3 g |
| 3-(2',5'-Dihydroxy-4'-methylphenyl)-propionic acid | 1.5 g | — |
| 3-(2',5'-Dihydroxyphenyl)-propionic acid | — | 1 g |
| Monoethanolamine q.s.p. | pH 8.2 | pH 8.2 |
| Water q.s.p. | 100 g | 100 g |

When applied to hair which has been bleached beforehand, 100 g of one or other of these compositions, in the form of a thickened liquid, impart to the head of hair, after rinsing with water, a particularly uniform silverwhite shade.

EXAMPLE NO. 4

The following dyeing composition is prepared:

| | | |
|---|---|---|
| 1-(N-Methylamino)-2-nitro-4-[N,N-bis-($\beta$-hydroxyethyl)-amino]-benzene | 0.15 | g |
| 1-Hydroxy-3-nitro-4-[N-($\beta$-hydroxyethyl)-amino]-benzene | 0.004 | g |
| 1-Hydroxy-2,6-dimethyl-3-nitro-4-[N-($\beta$-hydroxyethyl)-amino]-benzene | 0.02 | g |
| Mixture of cetyl/stearyl alcohol and sodium alkyl-sulphate, sold under the name "Sinnovax SX" by Messrs. Henkel | 2 | g |
| Linear fatty alcohol ($C_{13}$–$C_{15}$) oxyethyleneated with 2.8 mols of ethylene oxide, sold under the name "Ukanil 25" by Messrs. P.U.K. | 3 | g |
| Linear fatty alcohol ($C_{13}$–$C_{15}$) oxyethyleneated with 7 mols of ethylene oxide, sold under the name "Ukanil 43" by Messrs. P.U.K. | 2 | g |
| Trimethylcetylammonium bromide | 1.5 | g |
| Ethylene glycol monoethyl ether | 10 | g |
| Monoethanolamine q.s.p. pH 8 | | |
| Homogentisic acid | 1.2 | g |
| Water q.s.p. | 100 | g |

90 g of this mixture and 10 g of the propellant mixture F.114/12 (43/57) are incorporated into an aerosol container.

About 20 g of this foam are applied to bleached hair. After 15 minutes, the head of hair is rinsed and dried and is uniformly dyed irridescent blond.

EXAMPLE NO. 5

The following dyeing composition is prepared:

| | | |
|---|---|---|
| 1-(N-Methylamino)-2-nitro-4-[N,N-bis-($\beta$-hydroxyethyl)-amino]-benzene | 0.08 | g |
| 1-Hydroxy-3-nitro-4-[N-($\beta$-hydroxyethyl)-amino]-benzene | 0.004 | g |
| 1-Hydroxy-2,6-dimethyl-3-nitro-4-[N-($\beta$-hydroxyethyl)-amino]-benzene | 0.004 | g |
| Copra diethanolamide | 1.8 | g |
| Lauric acid | 0.9 | g |
| Methyl para-hydroxybenzoate | 0.1 | g |
| Tartaric acid | 0.25 | g |
| Ethylene glycol monobutyl ether | 4 | g |
| Hydroxyethylcellulose sold under the name "Cellosize WP 4400" by Messrs. Union Carbide | 3 | g |
| Homogentisic acid | 1 | g |
| Monoethanolamine q.s.p. pH 8 | | |
| Water q.s.p. | 100 | g |

When applied for 25 minutes to hair which has been bleached beforehand, 100 g of this composition, in the form of a thickened liquid, impart to the head of hair, after rinsing with water, a particularly uniform irridescent beige blond shade.

EXAMPLE NO. 6

The following dyeing composition is prepared:

| | | |
|---|---|---|
| 1-(N-Methylamino)-2-nitro-4-[N,N-bis-($\beta$-hydroxyethyl)-amino]-benzene | 0.005 | g |
| CI Disperse Violet 4 (61.105) | 0.005 | g |
| CI Disperse Black 5 | 0.003 | g |
| 1-Amino-2-nitro-4-(N-methyamino)-benzene | 0.004 | g |
| Copra diethanolamide | 1.8 | g |
| Lauric acid | 0.9 | g |
| Methyl para-hydroxybenzoate | 0.1 | g |
| Tartaric acid | 0.25 | g |
| Ethylene glycol monobutyl ether | 4 | g |
| Hydroxyethylcellulose sold under the name "Cellosize WP 4400" by Messrs. Union Carbide | 3 | g |
| Gentisic acid | 1 | g |
| Monoethanolamine q.s.p. pH 8 | | |
| Water q.s.p. | 100 | g |

When applied for 25 minutes to hair which has been bleached beforehand, 100 g of this composition, in the form of a thickened liquid, impart to the head of hair, after rinsing with water, a particularly uniform very light blond shade.

EXAMPLE NO. 7

The following dyeing composition is prepared:

| | |
|---|---|
| 1-(N-Methylamino)-2-nitro-4-[N,N-bis-($\beta$-hydroxyethyl)-amino]-benzene | 0.1 g |
| CI Disperse Violet 4 (61.105) | 0.05 g |
| CI Disperse Violet 15 | 0.03 g |
| CI Disperse Black 5 | 0.02 g |
| 4-Nitro-meta-phenylenediamine | 0.02 g |
| 1-Hydroxy-3-nitro-4-[N-($\beta$-hydroxyethyl)-amino]-benzene | 0.02 g |
| Copra diethanolamide | 1.8 g |
| Lauric acid | 0.9 g |
| Methyl para-hydroxybenzoate | 0.1 g |
| Tartaric acid | 0.25 g |
| Ethylene glycol monobutyl ether | 4 g |
| Hydroxyethylcellulose sold under the name "Cellosize WP 4400" by Messrs. Union Carbide | 3 g |
| Gentisic acid | 1 g |
| Monoethanolamine q.s.p. pH 8 | |
| Water q.s.p. | 100 g |

When applied for 25 minutes to hair which has been bleached beforehand, 100 g of this composition, in the form of a thickened liquid, impart to the head of hair, after rinsing with water, a particularly uniform ashen beige shade.

EXAMPLE No. 8

The following dyeing composition is prepared:

| | |
|---|---|
| 1-(N-Methylamino)-2-nitro-4-[N-methyl-N-($\beta$-hydroxyethyl)-amino]-benzene | 0.05 g |
| 1-Hydroxy-2,6-dimethyl-3-nitro-4-[N-($\beta$-hydroxyethyl)-amino]-benzene | 0.05 g |
| 1-Hydroxy-3-nitro-4-[N-($\beta$-hydroxyethyl)-amino]-benzene | 0.01 g |
| Mixture of cetyl/stearyl alcohol and sodium alkyl-sulphate, sold under the name "Sinnovax SX" by Messrs. Henkel | 2 g |
| Linear fatty alcohol ($C_{13}$-$C_{15}$) oxyethyleneated with 2.8 mols of ethylene oxide, sold under the name "Ukanil 25" by Messrs. P.U.K. | 3 g |
| Linear fatty alcohol ($C_{13}$-$C_{15}$) oxyethylated with 7 mols of ethylene oxide, sold under the name "Ukanil 43" by Messrs. P.U.K. | 2 g |
| Trimethylcetylammonium bromide | 1.5 g |
| Ethylene glycol monoethyl ether | 10 g |
| Gentisic acid | 1 g |
| Monoethanolamine q.s.p. pH 8 | |
| Water q.s.p. | 100 g |

90 g of this mixture and 10 g of the propellant mixture F.114/12 (43/57) are incorporated into an aerosol container. The product obtained retains its good dyeing properties for several months.

About 20 g of this foam are applied to moderately bleached hair. After 15 minutes, the head of hair is rinsed and dried and is uniformly dyed golden beige.

EXAMPLE NO. 9

| | |
|---|---|
| 1-(N-Methylamino)-2-nitro-4-(N,N-bis-($\beta$-hydroxyethylamino)-benzene | 0.055 g |
| CI Disperse Violet 4 (61105) | 0.03 g |
| 1-Amino-2-nitro-4-(N-methylamino)-benzene | 0.002 g |
| CI Disperse Black 5 | 0.01 g |
| 2-Methoxy-4-nitro-($\beta$-hydroxyethylamino)-benzene | 0.005 g |
| Lauryl diethanolamide | 1.1 g |
| Lauric acid | 1 g |
| Propylparahydroxy benzoate | 0.05 g |
| Methylparahydroxy benzoate | 0.1 g |
| Tartaric acid | 0.25 g |
| Propylene glycol | 1 g |
| 2-[(2',5'-dihydroxy-4'-methyl)phenyl] acetic acid | 0.8 g |
| Hydroxyethylcellulose sold under the name "Cellosize WP 3" by Messrs. Carbide and Carbon | 5 g |
| Ethyleneglycol monobutyl ether | 2.8 g |
| Monoethanolamine qsp | pH 9 |
| Water qsp | 100 g |

This composition, applied to bleached hair enables one to obtain, after leaving it for 25 minutes and rinsing with water, an ivory blonde shade.

EXAMPLE NO. 10

| | |
|---|---|
| 1-($\beta$-Hydroxyethyloxy)-3-nitro-4-amino benzene | 0.09 g |
| 1-Methoxy-3-nitro-4-(N-$\beta$-hydroxyethylamino)-benzene | 0.06 g |
| Cetylstearyl alcohol containing 20% of alcohol oxyethylenated with 15 E.O. sold under the name "Sinnowax AO" by Messrs. Henkel | 2 g |
| Linear fatty alcohol ($C_{13}$-$C_{15}$) oxyethylenated with 2.8 moles of ethylene oxide sold under the name "Ukanil 25" by Messrs. PUK | 3 g |
| Linear alcohol ($C_{13}$-$C_{15}$) oxyethylenated with 7 moles of ethylene oxide sold under the name "Ukanil 43" by Messrs PUK | 2 g |
| Trimethylcetylammonium bromide | 1.5 g |
| Ethyleneglycol monoethyl ether | 10 g |
| 2-[(2',5'-dihydroxy-3',4'-dimethyl)phenyl]-acetic acid | 2.3 g |
| Monoethanolamine qsp | pH 7 |
| Water qsp | 100 g |

This composition, applied to bleached hair, enables one to obtain, after leaving it for 10 minutes and rinsing with water, a golden copperish shade.

We claim:

1. A composition suitable for dyeing keratin fibres, comprising in an aqueous solution from about 0.005 to about 5% by weight of at least one direct dyestuff and from about 0.1 to about 10% by weight of an acid or salt of a compound having the formula:

$$\begin{array}{c} \text{OH} \\ R_1 \underset{R_2}{\underset{|}{\bigcirc}} (CH_2)_n - COOX \\ \text{OH} \end{array}$$

in which $R_1$ and $R_2$ are identical or different and denote hydrogen or a straight- or branched-chain alkyl group of 1 to 4 carbon atoms, X denotes hydrogen, an alkali metal, ammonium, or an alkanolamine radical, and n is 0 or an integer from 1 to 4.

2. A composition according to claim 1 in which $R_1$ or $R_2$ denotes a methyl, ethyl or propyl group and X denotes sodium, potassium, a monoethanolamine, diethanolamine or triethanolamine radical.

3. A composition according to claim 1 in which at least one of $R_1$ and $R_2$ denotes the said alkyl group.

4. A composition according to any one of claims 1 to 3, in which the said acid is selected from the group consisting of 3-(2',5'-dihydroxy-4'-methylphenyl)-propionic acid, 2-[(2',5'-dihydroxy-4'-methyl)phenyl]-acetic acid and 2-[(2',5'-dihydroxy-3',4'-dimethyl)-phenyl]-acetic acid.

5. A composition according to claim 1 in which the said acid is selected from the group consisting of gentisic acid, homogentisic acid and 3-(2',5'-dihydroxyphenyl)propionic acid.

6. A composition according to claim 1 which contains 0.5 to 3% by weight of an acid or a salt thereof, of formula (I).

7. A composition according to claim 1 in which the direct dyestuff is a nitro benzene derivative, an azo dyestuff or an anthraquinone dyestuff.

8. A composition according to claim 1 which contains 0.01 to 3% by weight of direct dyestuff.

9. A composition according to claim 1 wherein the aqueous solution further contains an alcohol, glycol or glycol ether solvent, in an amount from 0.5 to 20% by weight.

10. A composition according to claim 9 which contains 2 to 10% by weight of said solvent.

11. A composition according to claim 1 which also comprises an anionic, cationic, non-ionic, or amphoteric surface-active agent, in an amount from 0.5 to 50% by weight.

12. A composition according to claim 11 which contains 1 to 20% by weight of said surface-active agent.

13. A composition according to claim 1 which also comprises a fatty amide at a concentration of 0.5 to 10% by weight, a higher fatty alcohol at a concentration of 0.5 to 10% by weight, and or a thickener at a concentration of 0.5 to 15% by weight.

14. A composition according to claim 1, which also comprises monoethanolamine, diethanolamine, triethanolamine, ammonia, ammonium carbonate, potassium carbonate or sodium carbonate, or sodium hydroxide as an alkalizing agent.

15. A composition according to claim 14 which also comprises phosphoric, hydrochloric, tartaric, acetic, lactic or citric acid as acidifying agent.

16. A composition according to claim 1 which also comprises an adjuvant selected from the group consisting of perfumes, preservatives, sequestering agents and mixtures thereof.

17. A composition according to claim 1 which has a pH of 5 to 10.

18. A composition according to claim 17 which has a pH of 6 to 9.5.

19. A composition according to claim 18 which has a pH of 7 to 9.

20. A composition according to claim 1 which is a thickened liquid, foaming liquid or aerosol foam.

21. Process for dyeing human hair which comprises applying an effective amount of a composition as defined in claim 1 to the hair after it has been freshly bleached, allowing it to act for 5 to 30 minutes and then rinsing and drying the hair.

22. A process according to claim 21, in which the hair has been freshly bleached with an ammoniacal solution of hydrogen peroxide.

23. A process according to claim 22, in which the ammoniacal solution also contains ammonium persulphate, sodium persulphate or potassium persulphate.

* * * * *